(12) United States Patent
Chen et al.

(10) Patent No.: US 11,952,498 B2
(45) Date of Patent: Apr. 9, 2024

(54) COLORED FUNCTIONALIZED [2,2] PARACYCLOPHANE AND COLORED CHEMICAL FILM

(71) Applicant: National Taiwan University, Taipei (TW)

(72) Inventors: Hsien-Yeh Chen, Taipei (TW); Sheng-Tung Huang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 577 days.

(21) Appl. No.: 17/167,234

(22) Filed: Feb. 4, 2021

(65) Prior Publication Data

US 2022/0195199 A1    Jun. 23, 2022

(30) Foreign Application Priority Data

Dec. 18, 2020   (TW) .................................. 109145012

(51) Int. Cl.
| | | |
|---|---|---|
| C07C 25/22 | (2006.01) | |
| C07C 211/61 | (2006.01) | |
| C07C 255/58 | (2006.01) | |
| C07D 221/14 | (2006.01) | |
| C08G 61/02 | (2006.01) | |
| C09B 69/10 | (2006.01) | |

(52) U.S. Cl.
CPC ............ *C09B 69/109* (2013.01); *C07C 25/22* (2013.01); *C07C 211/61* (2013.01); *C07C 255/58* (2013.01); *C07D 221/14* (2013.01); *C08G 61/025* (2013.01); *C07C 2603/84* (2017.05)

(58) Field of Classification Search
USPC ........................................................ 528/396
See application file for complete search history.

(56) References Cited

U.S. PATENT DOCUMENTS 9,972,791 B2 *   5/2018  Buchwald .............. C09K 11/06

FOREIGN PATENT DOCUMENTS

TW            201527279 A       7/2015

OTHER PUBLICATIONS

Search Report appended to an Office Action, which was issued to Taiwanese counterpart application No. 109145012 by the TIPO on Jun. 18, 2021 with an English translation thereof (2 pages).
Petra Lennartz, et al., "Synthesis of Planar Chiral Carbazole Derivatives Bearing a [2.2]Paracyclophane Skeleton", Israel Journal of Chemistry, vol. 52, No. 1-2, 2012, Feb. 14, 2012, pp. 171-179.

* cited by examiner

*Primary Examiner* — Terressa Boykin
(74) *Attorney, Agent, or Firm* — Hamre, Schumann, Mueller & Larson, P.C.

(57) ABSTRACT

Disclosed herein are a colored functionalized paracyclophane represented by Formula (I) and a colored chemical film represented by Formula (II):

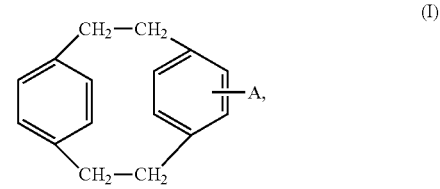

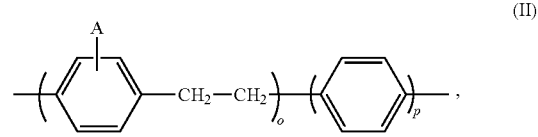

wherein A, o, and p in Formula (I) and Formula (II) are as defined herein. The colored chemical film may be formed from the colored functionalized [2,2]paracyclophane by chemical vapor deposition.

8 Claims, No Drawings

COLORED FUNCTIONALIZED [2,2] PARACYCLOPHANE AND COLORED CHEMICAL FILM

CROSS-REFERENCE TO RELATED APPLICATION

This application claims priority of Taiwanese Invention Patent Application No. 109145012, filed on Dec. 18, 2020.

FIELD

The disclosure relates to a [2,2]paracyclophane and a chemical film formed thereof, and more particularly to a colored functionalized [2,2]paracyclophane and a colored chemical film formed thereof.

BACKGROUND

A poly-para-xylylene film prepared by virtue of chemical vapor deposition of [2,2]paracyclophane is compatible with substrates of various materials and surface structures, and does not cause damage to the original mechanical property of the substrate. Additionally, [2,2]paracyclophane and the poly-para-xylylene film formed thereof both share a characteristic of biocompatibility. Therefore, the poly-para-xylylene film is widely used in the biomedical field as a surface coating of medical equipment.

Nevertheless, conventional poly-para-xylylene films, e.g., commercialized parylene N, parylene C, parylene HT, and parylene D are all available as transparent and colorless poly-para-xylylene films, and thus, after a poly-para-xylylene film is formed by chemical vapor deposition, the quality of such poly-para-xylylene film cannot be determined by the naked eye unless expensive inspection instruments are being utilized, which is not only time-consuming and costly, but also impossible to immediately adjust the process conditions accordingly by inspecting the quality of the poly-para-xylylene film straightaway after the process ended. Moreover, since the poly-para-xylylene film is transparent and colorless, the naked eye is unable to distinguish whether the film has been coated or not yet coated, which might result in the coated film being coated repeatedly, or the uncoated film being left uncoated. The colorless feature of the poly-para-xylylene film is also disadvantageous for medical personnel who need to inspect medical equipment using naked eye before conducting medical treatment, and thus, there is a risk of a medical equipment that is uncoated or that has a torn film being implanted into the human body.

SUMMARY

Therefore, an object of the disclosure is to provide a colored functionalized [2,2]paracyclophane for forming a colored chemical film that can alleviate at least one of the drawbacks of the prior art.

According to the disclosure, there is provided a colored functionalized [2,2]paracyclophane having formula (I):

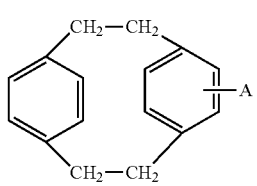

(I)

wherein A represents a group having formula (A1), formula (A2), or formula (A3):

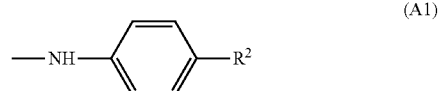

(A1)

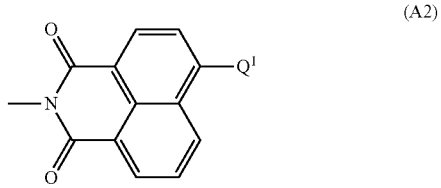

(A2)

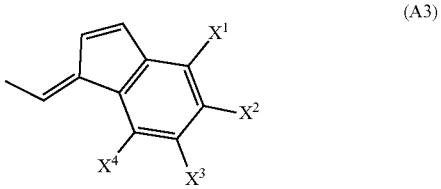

(A3)

wherein, $R^1$ and $R^2$ each independently represent —H, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$NO_2$, —CN, or —$SO_2CH_3$, with the proviso that $R^1$ and $R^2$ are not —H at the same time;

$Q^1$ represents

or —$N(C_nH_{2n+1})(C_mH_{2m+1})$, wherein m and n each independently represent an integer of 1 to 4;

$X^1$, $X^2$, $X^3$, and $X^4$ each independently represent —H, —F, —Cl, —Br, or —I, with the proviso that $X^1$, $X^2$, $X^3$, and $X^4$ are not —H at the same time.

The other object of the disclosure is to provide a colored chemical film that can alleviate at least one of the drawbacks of the prior art.

According to the disclosure, there is provided a colored chemical film including a functionalized poly-p-xylylene having formula (II):

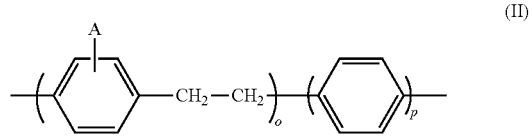

(II)

wherein, o and p each independently represent an integer of 2 to 10,000; and

A represents a group having formula (A1), formula (A2), or formula (A3):

(A1)

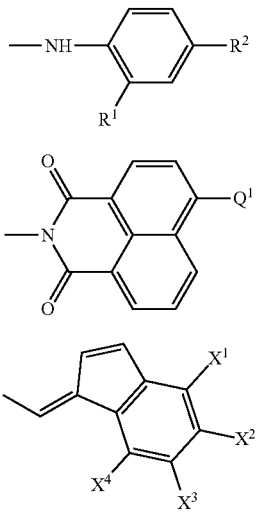

wherein,
R$^1$ and R$^2$ each independently represent —H, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —NO$_2$, —CN, or —SO$_2$CH$_3$, with the proviso that R$^1$ and R$^2$ are not —H at the same time;
Q$^1$ represents

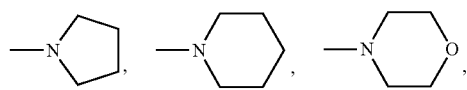

or —N(C$_n$H$_{2n+1}$)(C$_m$H$_{2m+1}$), wherein m and n each independently represent an integer of 1 to 4; and
X$^1$, X$^2$, X$^3$, and X$^4$ each independently represent —H, —F, —Cl, —Br, or —I, with the proviso that X$^1$, X$^2$, X$^3$, and X$^4$ are not —H at the same time.

DETAILED DESCRIPTION

A colored functionalized [2,2]paracyclophane of the disclosure is represented by formula (I):

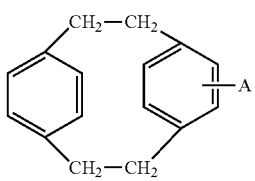

wherein,
A represents a group having formula (A1), formula (A2), or formula (A3):

(A1)

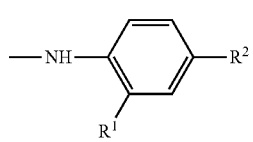

(A2)

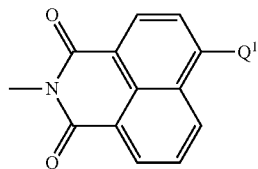

(A3)

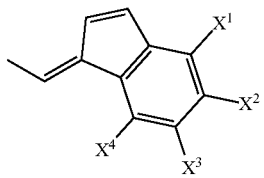

In formula (A1), R$^1$ and R$^2$ each independently represent —H, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, CHI$_2$, —CH$_2$I, —NO$_2$, —CN, or —SO$_2$CH$_3$, with the proviso that R$^1$ and R$^2$ are not —H at the same time. In some embodiments, R$^1$ and R$^2$ each independently represent —H, —F, —CF$_3$, —CN, or —SO$_2$CH$_3$, with the proviso that R$^1$ and R$^2$ are not —H at the same time. In some embodiments, R$^1$ represents —H, and R$^2$ represents —NO$_2$ or —CN. In some embodiments, R$^1$ represents —F, and R$^2$ represents —H.

In formula (A2), Q$^1$ represents

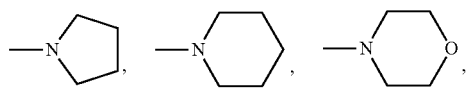

or —N(C$_n$H$_{2n+1}$)(C$_m$H$_{2m+1}$), wherein m and n each independently represent an integer of 1 to 4. In some embodiments, Q$^1$ represents

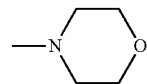

or —N(C$_n$H$_{2n+1}$)(C$_m$H$_{2m+1}$), wherein m and n each independently represent an integer of 1 to 2. In some embodiments, Q$^1$ represents

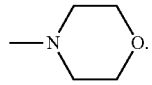

In formula (A3), X$^1$, X$^2$, X$^3$, and X$^4$ each independently represent —H, —F, —Cl, —Br, or —I, with the proviso that X$^1$, X$^2$, X$^3$, and X$^4$ are not —H at the same time. In some embodiments, X$^1$, X$^2$, X$^3$, and X$^4$ each independently represent —H or —F, with the proviso that X$^1$, X$^2$, X$^3$, and X$^4$ are not —H at the same time.

A colored chemical film of the disclosure, including a functionalized poly-p-xylylene is represented by formula (II):

(II)

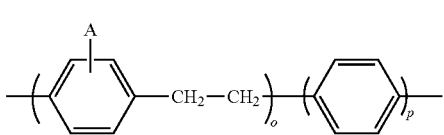

wherein, o and p each independently represent an integer of 2 to 10,000; and

A represents a group having formula (A1), formula (A2) or formula (A3):

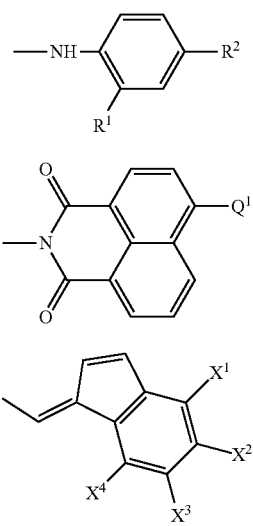

In formula (A1), $R^1$ and $R^2$ each independently represent —H, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$NO_2$, —CN, or —$SO_2CH_3$, with the proviso that $R^1$ and $R^2$ are not —H at the same time. In some embodiments, $R^1$ and $R^2$ each independently represent —H, —F, —$CF_3$, —CN, or —$SO_2CH_3$, with the proviso that $R^1$ and $R^2$ are not —H at the same time. In some embodiments, $R^1$ represents —H, and $R^2$ represents —$NO_2$ or —CN. In some embodiments, $R^1$ represents —F, and $R^2$ represents —H.

In formula (A2), $Q^1$ represents

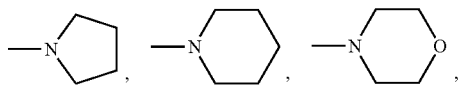

or —$N(C_nH_{2n+1})(C_mH_{2m+1})$, wherein m and n each independently represent an integer of 1 to 4. In some embodiments, $Q^1$ represents

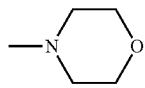

or —$N(C_nH_{2n+1})(C_mH_{2m+1})$, wherein m and n each independently represent an integer of 1 to 2. In some embodiments, $Q^1$ represents

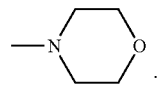

In formula (A3), $X^1$, $X^2$, $X^3$, and $X^4$ each independently represent —H, —F, —Cl, —Br, or —I, with the proviso that $X^1$, $X^2$, $X^3$, and $X^4$ are not —H at the same time. In some embodiments, $X^1$, $X^2$, $X^3$, and $X^4$ each independently represent —H or —F, with the proviso that $X^1$, $X^2$, $X^3$, and $X^4$ are not —H at the same time.

A method of forming a colored functionalized [2,2]paracyclophane into a colored chemical film may be conducted by, e.g., chemical vapor deposition, in which the colored functionalized [2,2]paracyclophane is subjected to sublimation, cracking, and deposition sequentially, such that the colored chemical film is formed on a substrate. The temperature range for the sublimation is 80° C. to 150° C., the temperature range for the cracking is 500° C. to 850° C., the temperature range for the deposition is −10° C. to 50° C., the pressure range for the chemical vapor deposition is 20 mTorr to 500 mTorr, and the flow rate range of an inert gas for the chemical vapor deposition is 5 sccm to 200 sccm. The material of the substrate may be, but is not limited to, silicon, glass, metal, or polymer.

Examples of the disclosure will be described hereinafter. It is to be understood that these examples are exemplary and explanatory and should not be construed as a limitation to the disclosure.

Example 1

Preparation of a Colored Functionalized [2,2]paracyclophane (Compound I-1)

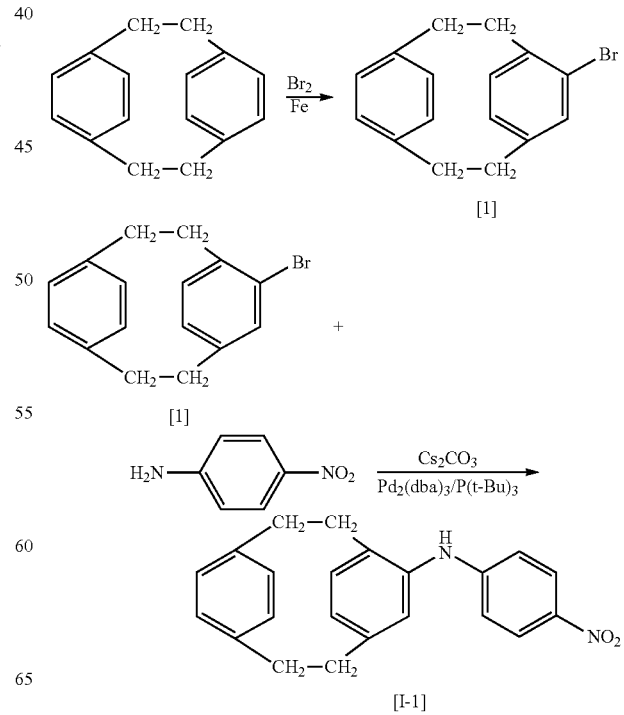

Synthesis of Compound 1

The synthesis of Compound 1 was conducted under a nitrogen environment with light isolation using aluminum foil. First, 1.17 mL (22.68 mmole) of liquid bromine was added into 225 mL of dichloromethane to obtain a mixture solution. Next, 22.5 mL of the mixture solution was added to 600 mg of iron powder, followed by reaction for 1.5 hours to obtain a reaction mixture. Then, 4.5 g (21.60 mmole) of [2,2]paracyclophane dissolved in 216 mL of dichloromethane was slowly and completely dropped into the reaction mixture, followed by reaction for 20 minutes. After that, a remaining portion of the mixture solution was dropped completely, followed by reaction for 1 hour, and then 400 mL of a saturated solution of sodium bisulfite was added to stop the reaction, thereby obtaining a coarse product. The coarse product was extracted 2 times with 400 mL of dichloromethane each time, and an organic phase was collected therefrom. The organic layer was dehydrated with anhydrous magnesium sulfate, and the solvent in the organic layer was removed using a rotary evaporator, followed by purification using column chromatography (stationary phase: silica gel 60, eluent: n-hexane, retention factor (Rf)=0.4), so as to obtain a white powder, i.e., Compound 1 (4.23 g, yield: 68%).

Compound 1 was identified using a nuclear magnetic resonance spectrometer (BRUKER Avance II™ 300 MHz). The result is shown below.

$^1$H-NMR (300 MHz, CDCl$_3$), δ(ppm): 7.12 (dd, J=8.1, 2.1 Hz, 1H), 6.56-6.42 (m, 6H), 3.44 (dtd, J=11.6, 2.7, 2.1 Hz, 1H), 3.23-2.75 (m, 7H).

Synthesis of Compound I-1

The synthesis of Compound I-1 was conducted under a nitrogen environment. Compound 1 (2.0 g, 6.96 mmole), cesium carbonate (Cs$_2$CO$_3$, 7.72 g, 23.69 mmole), tri-tert-butylphosphine (P(t-Bu$_3$), 1.8 mL, 0.35 mmole), 4-nitroaniline (1.92 g, 13.92 mmole), and tris(dibenzylideneacetone)dipalladium(0)(Pd$_2$(dba)$_3$, 0.16 g, 0.175 mmole) were dissolved in 60 mL of o-xylene, and then heated to a temperature of 135° C., followed by reaction at such temperature for 24 hours to obtain a coarse product. The coarse product was filtered with filter paper and a cake was collected therefrom. The cake was extracted 3 times with 60 mL of ethyl acetate each time, and an organic layer was collected therefrom. The organic layer was dehydrated with anhydrous magnesium sulfate, and the solvent in the organic layer was removed using a rotary evaporator, followed by purification using column chromatography (stationary phase: silica gel 60, eluent: n-hexane/ethyl acetate=3/1, Rf=0.4), so as to obtain a yellow powder, i.e., Compound I-1 (0.56 g, yield: 23%).

Compound I-1 was identified using a nuclear magnetic resonance spectrometer (BRUKER Avance II™ 300 MHz), a FT-Infrared spectrometer (FT-IR, HORIBA FT-720), a mass spectrometer (Hiden Analytical HAL RC 511), and a melting point apparatus (MBA, METTLER TOLEDO MP70). The results are shown below.

$^1$H-NMR (300 MHz, CDCl$_3$), δ(ppm): 8.08 (d, J=9.0 Hz, 2H), 6.87 (dd, J=6.3, 1.5 Hz, 1H), 6.78 (dd, J=5.4, 1.8 Hz, 2H), 6.60-6.43 (m, 5H), 6.13 (s, 1H), 5.94 (s, 1H), 3.10-2.83 (m, 7H), 2.78-2.68 (m, 1H).

$^{13}$C-NMR (CDCl$_3$, 300 MHz): 150.0, 141.8, 139.6, 139.5, 139.2, 137.0, 136.2, 134.3, 133.8, 133.1, 131.3, 130.2, 128.9, 127.2, 126.1, 113.0, 35.1, 34.7, 34.0, 33.7.

ESI-MS(ESI$^+$): m/z (%)=345.16 (100) [M+1].

FT-IR(KBr): v/cm$^{-1}$=3350, 3065, 3007, 2928, 2892, 2853, 1600, 1498, 1474, 1323, 1288, 1180, 1111, 841, 751.

Melting point: 186° C.-187° C.

Preparation of a Colored Chemical Film

Compound I-1 was placed into a chemical vapor deposition equipment that was fed with argon (flow rate: 50 sccm) continuously such that the pressure inside the chemical vapor deposition equipment was controlled at 380 mTorr. After that, Compound I-1 was sublimated at a sublimation temperature of 110° C., and then cracked at a cracking temperature of 650° C. After that, the cracked Compound I-1 was deposited on a gold-plated silicon substrate (commercially available from Gredmann Taiwan Ltd.) at a deposition temperature of 30° C., and then polymerized to form a colored chemical film including a functionalized poly-p-xylylene having formula (II-1):

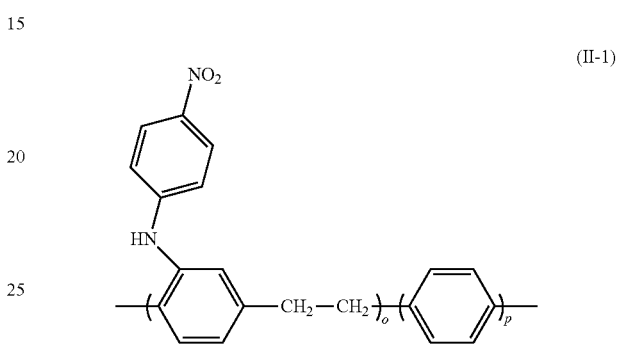

(II-1)

wherein o and p each independently represent an integer of 2 to 10,000.

Example 2

Preparation of a Colored Functionalized [2,2]paracyclophane (Compound I-2)

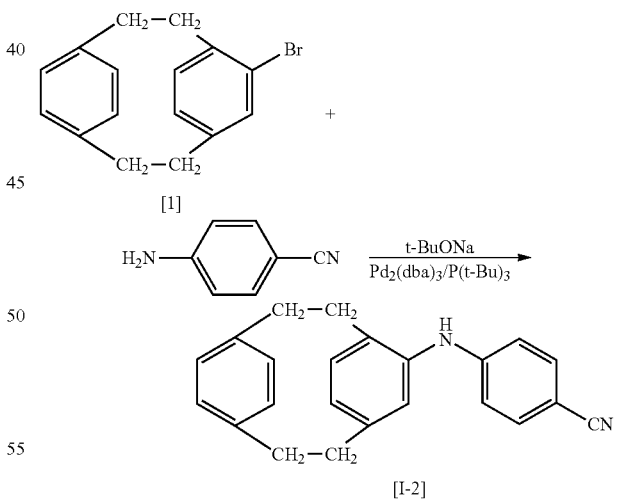

Synthesis of Compound I-2

The synthesis of Compound I-2 was conducted under a nitrogen environment. Compound 1 (1.0 g, 3.48 mmole), sodium tert-butoxide (t-BuONa, 0.5 g, 0.52 mmole), P(t-Bu$_3$) (180 μL, 36 μmole), 4-aminobenzonitrile (0.41 g, 3.48 mmole), and Pd$_2$(dba)$_3$ (32 mg, 35 μmole) were dissolved in 25 mL of o-xylene and heated to a temperature of 135° C., followed by reaction at such temperature for 12 hours. After that, 25 mL of 10% aqueous solution of ammonium chloride was added to stop the reaction, thereby obtaining a coarse product. The coarse product was extracted 3 times with 25 mL of ethyl acetate each time, and an organic layer was collected therefrom. The organic layer was dehydrated with anhydrous magnesium sulfate, and the solvent in the organic layer was removed using a rotary evaporator, followed by purification using column chromatography (stationary phase: silica gel 60, eluent: n-hexane/ethyl acetate=3/1, Rf=0.4), so as to obtain a yellow powder, i.e., Compound I-2 (0.24 g, yield: 21%).

Compound I-2 was identified using the same instruments as those for Compound I-1. The results are shown below.

$^1$H-NMR (300 MHz, CDCl$_3$), δ(ppm): 7.42 (d, J=8.7 Hz, 2H), 6.88 (dd, J=8.1, 1.8 Hz, 1H), 6.80 (d, J=8.7 Hz, 2H), 6.57 (dd, J=7.8, 1.8 Hz, 1H), 6.50-6.41 (m, 4H), 5.90 (s, 2H), 3.09-2.82 (m, 7H), 2.75-2.65 (m, 1H). $^{13}$C-NMR (300 MHz, CDCl$_3$): 141.7, 139.5, 139.1, 137.3, 136.1, 134.0, 133.7, 133.6, 132.4, 131.2, 129.7, 128.5, 127.2, 120.0, 114.1, 101.0, 35.1, 34.7, 34.0, 33.7.

ESI-MS(ESI$^+$): m/z (%)=325.17 (100) [M+1].

FT-IR(KBr): ν/cm$^{-1}$=3369, 3030, 2923, 3093, 2860, 2225, 1611, 1582, 1501, 1486, 1431, 1320, 1173, 1114, 1020, 974, 880, 818, 647, 493.

Melting point: 168° C.-169° C.

Preparation of a Colored Chemical Film

Compound I-2 was placed into a chemical vapor deposition equipment that was fed with argon (flow rate: 50 sccm) continuously such that the pressure inside the chemical vapor deposition equipment was controlled at 380 mTorr. After that, Compound I-2 was sublimated at a sublimation temperature of 120° C., and then cracked at a cracking temperature of 700° C. After that, the cracked Compound I-2 was deposited on a gold-plated silicon substrate at a deposition temperature of 30° C., and then polymerized to form a colored chemical film including a functionalized poly-p-xylylene having formula (II-2):

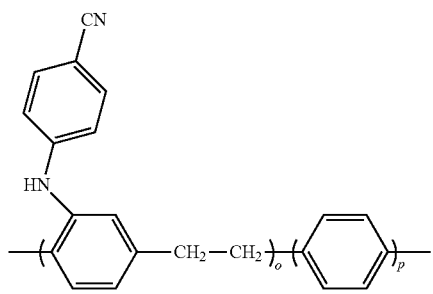

(II-2)

wherein o and p each independently represent an integer of 2 to 10,000.

Example 3

Preparation of a Colored Functionalized [2,2]paracyclophane (Compound I-3)

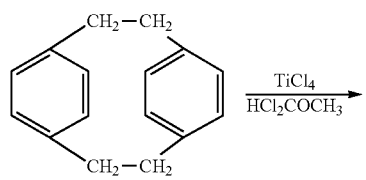

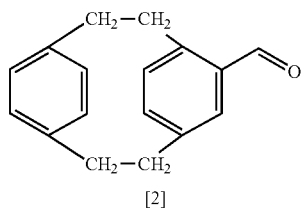

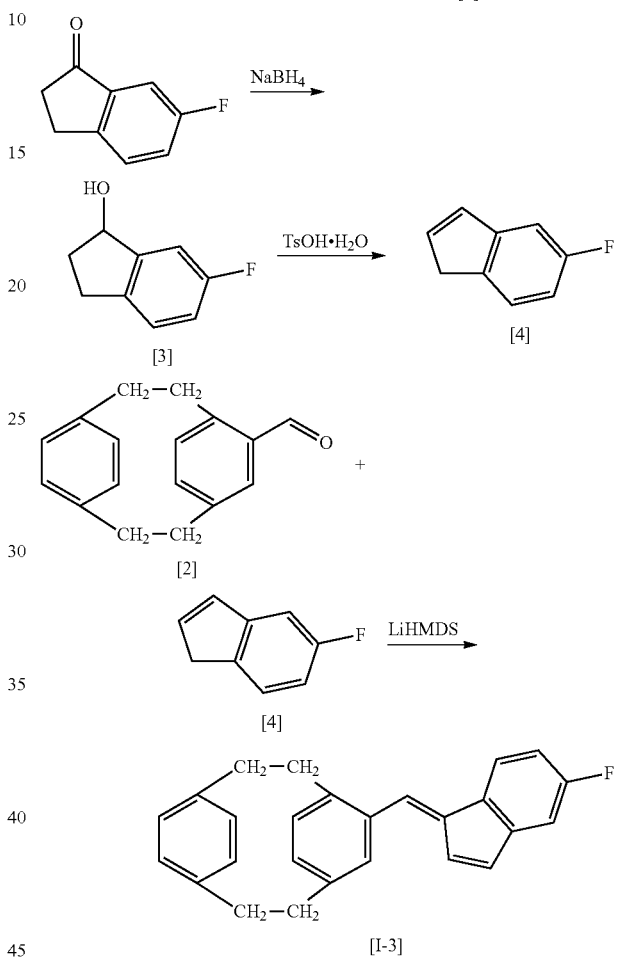

Synthesis of Compound 2

The synthesis of Compound 2 was conducted under a nitrogen environment. First, 1,1-dichlorodimethyl ether (220 μL, 2.44 mmole) was dissolved in 5 mL of dichloromethane to obtain a mixed liquor. Next, under an ice bath environment of 0° C., titanium (IV) chloride (530 μl, 4.8 mmole) was added into the mixed liquor, followed by reaction for 30 minutes to obtain a reaction mixture. After that, 0.5 g (2.4 mmole) of [2,2]paracyclophane dissolved in 15 mL of dichloromethane was dropped slowly and completely into the reaction mixture, followed by reaction for minutes. Then, water was added to stop the reaction, thereby obtaining a coarse product. The coarse product was extracted 3 times with 20 mL of dichloromethane each time, and an organic layer was collected therefrom. The organic layer was dehydrated with anhydrous magnesium sulfate, and the solvent in the organic layer was removed using a rotary evaporator, so as to obtain a white powder, i.e., Compound 2.

Compound 2 was identified using the same instrument as that for Compound 1. The result is shown below.

$^1$H-NMR (300 MHz, CDCl$_3$), δ (ppm): 9.93 (s, 1H), 7.00 (d, J=1.8 Hz, 1H), 6.71 (dd, J=6.0, 1.8 Hz, 1H), 6.58-6.34 (m, 5H), 4.12-4.04 (m, 1H), 3.29-2.88 (m, 7H).

Synthesis of Compound 3

First, 1.5 g (10.00 mmole) of 6-fluoro-1-indanone was dissolved in 40 mL of ethanol to obtain a mixed liquor. Next, under an ice bath environment of 0° C., the mixed liquor was gradually added into 0.38 g (10.00 mL) of sodium borohydride (NaBH$_4$) in 10 portions. After one portion of the mixed liquor was added, a reaction for 10 minutes was conducted before adding another portion. After all of the mixed liquor were added, the ice bath was removed, followed by reaction under room temperature for 3 hours to obtain a coarse product. The organic solvent in the coarse product was removed using a rotary evaporator, and then the coarse product was extracted 2 times with mL of ethyl acetate each time to collect the organic layer therefrom. The organic layer was dehydrated with anhydrous magnesium sulfate and the solvent in the organic layer was removed using a rotary evaporator, followed by purification using column chromatography (stationary phase: silica gel 60, eluent: n-hexane/ethyl acetate=6/1, Rf=0.3), so as to obtain a transparent oily substance, i.e., Compound 3 (1.12 g, yield: 73%).

Compound 3 was identified using the same instrument as that for Compound 1. The result is shown below.

$^1$H-NMR (300 MHz, DMSO), δ(ppm): 7.21 (dd, J=8.1, 2.4 Hz, 1H), 7.08-6.95 (m, 2H), 5.31 (d, J=6.0 Hz, 1H), 5.01 (dd, J=12.9, 6.6 Hz, 1H), 2.90-2.82 (m, 1H), 2.80-2.60 (m, 1H), 2.40-2.30 (m, 1H), 1.84-1.72 (m, 1H).

Synthesis of Compound 4

First, 0.53 g (3.48 mmole) of Compound 3 and 0.07 g (0.35 mmole) of p-toluenesulfonic acid monohydrate (TsOH.H$_2$O) were added into 25 mL of toluene to obtain a mixture. Next, the mixture was refluxed to 110° C. using a Dean-Stark device, followed by reaction at such temperature for 1 hour to obtain a coarse product. After that, the coarse product was cooled to room temperature, and then washed 2 times with 25 mL of saturated solution of sodium hydrogen carbonate each time. Thereafter, the coarse product was dehydrated with anhydrous magnesium sulfate, followed by removal of an organic solvent using a rotary evaporator. Subsequently, the coarse product was purified using column chromatography (stationary phase: Silica gel 60, eluent: n-hexane/ethyl acetate=6/1, Rf=0.9), so as to obtain a transparent oily substance, which was Compound 4 (0.36 g, yield: 77%).

Compound 4 was identified using the same instrument as that for Compound 1. The result is shown below.

$^1$H-NMR (300 MHz, CDCl$_3$), δ(ppm): 7.36 (dd, J=8.1, 5.1 Hz, 1H), 7.07 (dd, J=9.0-2.4 Hz, 1H), 6.90-6.81 (m, 2H), 6.62 (d, J=5.7 Hz, 1H), 3.35 (s, 2H).

Synthesis of Compound I-3

The synthesis of Compound I-3 was conducted under a nitrogen environment. First, 56 mg (0.42 mmole) of Compound 4 and 0.63 mL (0.63 mmole) of lithium bis(trimethylsilyl)amide (LiHMDS) were dissolved in 1.5 mL tetrahydrofuran, followed by reaction for 30 minutes to obtain a reaction mixture. Then, a solution formed by dissolving 0.1 g (0.42 mmole) of Compound 2 in 2 mL of tetrahydrofuran was slowly and completely dropped into the reaction mixture to allow a reaction to proceed for 12 hours, followed by adding a saturated solution of ammonium chloride to end the reaction, so as to obtain a coarse product. The coarse product was extracted 3 times with 5 mL of dichloromethane each time, and then dehydrated with anhydrous magnesium sulfate. Thereafter, the organic solvent in the coarse product was removed using a rotary evaporator, followed by purification using column chromatography (stationary phase: Silica gel 60, eluent: n-hexane/ethyl acetate=19/1, Rf=0.7), so as to obtain a yellow powder, i.e., Compound I-3 (43 mg, yield: 29%).

Compound I-3 was identified using the same instruments as those for Compound I-1. The results are shown below.

$^1$H-NMR (300 MHz, CDCl$_3$), δ (ppm): 7.49-7.46 (m, 2H), 7.25-7.20 (m, 1H), 7.03-6.93 (m, 2H), 6.86-6.77 (m, 1H), 6.65-6.54 (m, 6H), 6.45-6.43 (m, 1H), 3.64-3.56 (m, 1H), 3.23-2.87 (m, 7H).

$^{13}$C-NMR (300 MHz, CDCl$_3$), δ (ppm): 140.0, 139.8, 139.6, 139.4, 139.2, 136.5, 136.3, 136.1, 135.9, 135.2, 134.5, 133.4, 133.3, 133.1, 132.1, 133.0, 132.1, 130.8, 130.7, 128.7, 128.3, 127.9, 126.9, 35.4, 35.1, 34.8, 34.6.

ESI-MS (ESI$^+$): m/z (%)=352.16 (37) [M].

FT-IR (KBr): v/cm$^{-1}$=3052, 3021, 2922, 1614, 1591, 1515, 1483, 1365, 1330, 1268, 1183, 1161, 1125, 1107, 955, 929, 896, 836, 647, 49.

Melting point: 127° C.-128° C.

Preparation of a Colored Chemical Film

Compound I-3 was placed into a chemical vapor deposition equipment that was fed with argon (flow rate: 50 sccm) continuously such that the pressure inside the chemical vapor deposition equipment was controlled at 380 mTorr. Next, Compound I-3 was sublimated at a sublimation temperature of 130° C., and then cracked at a cracking temperature of 700° C. After that, the cracked Compound I-3 was deposited on a gold-plated silicon substrate at a deposition temperature of 50° C. and then polymerized to form a colored chemical film including a functionalized poly-p-xylylene having formula (II-3):

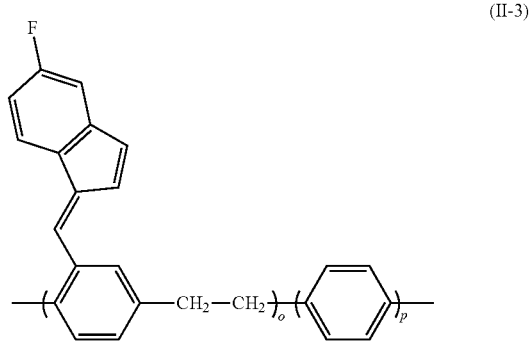

(II-3)

wherein o and p each independently represent an integer of 2 to 10,000.

Example 4

Preparation of a Colored Functionalized [2,2]paracyclophane (Compound I-4)

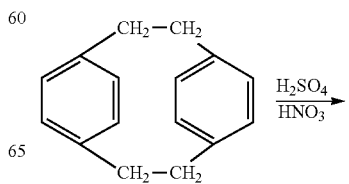

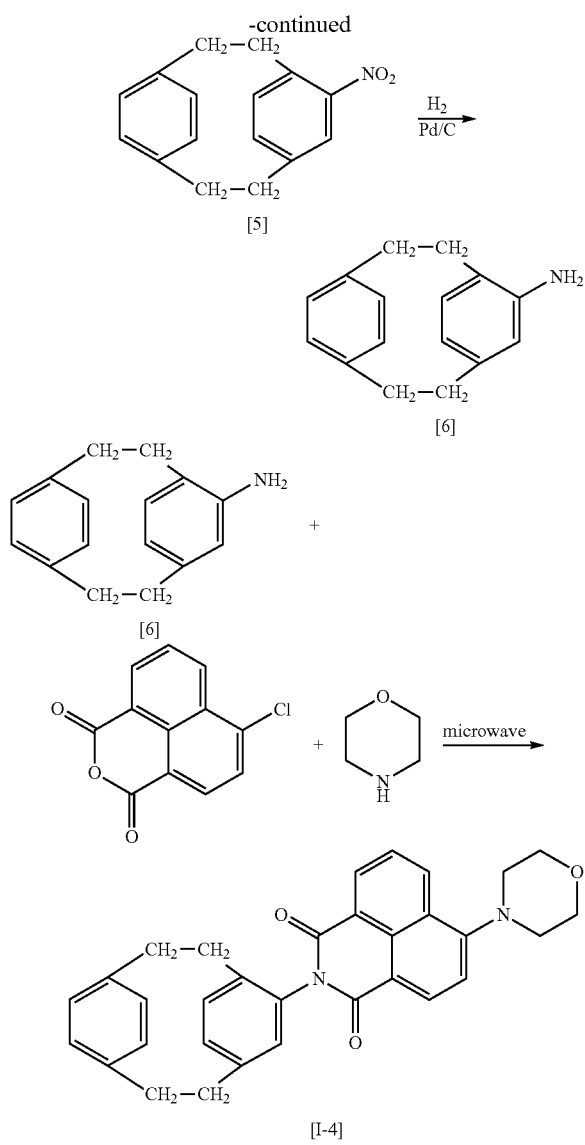

Synthesis of Compound 5

First, 4.4 mL (76.8 mmole) of sulfuric acid was dropped into 2.7 mL (38.4 mmole) of nitric acid to obtain a mixture solution. Next, 4.0 g (19.2 mmole) of [2,2]paracyclophane dissolved in 370 mL of dichloromethane was dropped slowly into the mixture solution, followed by reaction for 4 hours to obtain a coarse product. Thereafter, the organic solvent in the coarse product was removed with a rotary evaporator, and the coarse product was extracted for 4 times with 150 mL of ethyl acetate each time to collect an organic layer therefrom. The organic layer was dehydrated with anhydrous magnesium sulfate, and the solvent in the organic layer was removed using the rotary evaporator, followed by purification using column chromatography (stationary phase: silica gel 60, eluent: n-hexane/ethyl acetate=19/1, Rf=0.5), so as to obtain a yellow powder, i.e., Compound 5 (2.94 g, yield: 60%).

Compound 5 was identified using the same instrument as that for Compound 1. The result is shown below.

$^1$H-NMR (300 MHz, CDCl$_3$), δ(ppm): 7.19 (d, J=1.5 Hz, 2H), 6.77 (dd, J=8.1, 1.8 Hz, 1H), 6.61-6.55 (m, 4H), 6.66 (d, J=8.1 Hz, 1H), 4.05-3.97 (m, 1H), 3.21-2.82 (m, 6H), 2.90-2.15 (m, 1H).

Synthesis of Compound 6

First, 3.0 g (11.84 mmole) of Compound 5 and 180 mg of palladium on carbon (Pd/C) were dissolved in 160 mL of ethyl acetate, followed by reaction for 12 hours to obtain a coarse product. Next, the coarse product was filtered with 3 layers of filter paper, and a cake was collected therefrom. Then, the cake was added into a small amount of methanol, followed by recrystallization under an ice bath environment at −75° C., which was achieved by mixing dry ice and isopropanol. Subsequently, the formed crystal was purified by column chromatography (stationary phase: silica gel 60, eluent: n-hexane/ethyl acetate=3/1, Rf=0.7), so as to obtain a light yellow powder, i.e., Compound 6 (1.86 g, yield: 70%).

Compound 6 was identified using the same instrument as that for Compound 1. The result is shown below.

$^1$H-NMR (300 MHz, CDCl$_3$), δ(ppm): 7.15 (dd, J=7.8, 1.8 Hz, 1H), 6.56 (dd, J=7.8, 1.8 Hz, 1H), 6.37 (dd, J=7.8, 1.8 Hz, 2H), 6.24 (d, J=7.5, 1H), 6.11 (dd, J=7.8, 1.8 Hz, 2H), 5.36 (d, J=1.8 Hz, 1H), 3.44 (s, 2H), 3.14-2.89 (m, 6H), 2.84-2.75 (m, 1H), 2.70-2.60 (m, 1H).

Synthesis of Compound I-4

First, 50 mg (0.224 mmole) of Compound 6, 65 mg (0.279 mmole) of 4-chloro-1,8-naphthalic anhydride, and 0.03 mL (0.336 mmole) of morpholine were added into 0.25 mL of dimethyl sulfoxide to obtain a mixture. Next, the mixture was then placed in a CEM Discover focused microwave synthesizer, followed by reaction for 2 hours at 150 W microwave power and a temperature of 150° C., so as to obtain a coarse product. Thereafter, the coarse product was mixed with water, and then filtered with filter paper so as to collect a cake that was immersed in water continuously. After that, the cake was dissolved in dichloromethane, and then water was removed using anhydrous magnesium sulfate. Subsequently, an organic solvent was removed from the cake using a rotary evaporator, followed by purification using column chromatography (stationary phase: silica gel 60, eluent: n-hexane/ethyl acetate=3/1, Rf=0.4), so as to obtain a yellow powder, i.e., Compound I-4 (36 mg, yield: 33%).

Compound I-4 was identified using the same instruments as those for Compound I-1. The results are shown below.

$^1$H-NMR (300 MHz, CDCl$_3$), δ(ppm): 8.73 (dd, J=17.1, 7.2 Hz, 1H), 8.54-8.42 (m, 2H), 7.74 (dt, J=27.3, 8.1, 1H), 7.32-7.21 (m, 1H), 6.84-6.80 (m, 2H), 6.69 (s, 2H), 6.57-6.48 (m, 2H), 6.39 (d, J=7.5 Hz, 1H), 4.11-4.03 (m, 4H), 3.32-3.22 (m, 6H), 3.11-2.95 (m, 4H), 2.90-2.75 (m, 2H).

$^{13}$C-NMR (300 MHz, CDCl$_3$): 164.1, 163.6, 155.5, 138.8, 138.7, 138.5, 137.7, 134.7, 134.4, 134.1, 132.9, 132.7, 132.3, 131.8, 131.5, 131.3, 130.0, 128.4, 125.8, 123.9, 123.2, 117.5, 117.0, 114.9, 66.8, 53.2, 35.2, 35.1, 34.8, 31.0.

ESI-MS(ESI$^+$): m/z (%)=489.22 (85) [M+].

FT-IR(KBr): v/cm$^{-1}$=2956, 2924, 2854, 1771, 1728, 1697, 1587, 1516, 1451, 1398, 1346, 1300, 1260, 1117, 1086, 1015, 993, 916, 782, 730.

Melting point: 247° C.-248° C.

Preparation of a Colored Chemical Film

Compound I-4 was placed into a chemical vapor deposition equipment that was fed with argon (flow rate: 50 sccm) continuously such that the pressure inside the chemical vapor deposition equipment was controlled at 380 mTorr. Next, Compound I-4 was sublimated at a sublimation temperature of 125° C., and then cracked at a cracking temperature of 680° C. Thereafter, the cracked Compound I-4 was deposited on a gold-plated silicon substrate at a deposition temperature of 40° C., and then polymerized to form a colored chemical film including a functionalized poly-p-xylylene having formula (II-4):

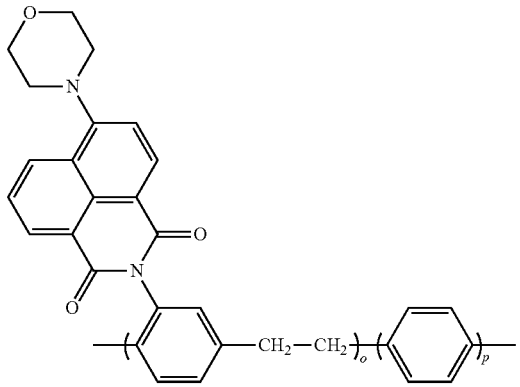

(II-4)

wherein o and p each independently represent an integer of 2 to 10,000.

Ultraviolet-Visible Spectroscopy (UV-Vis)

A UV-Vis spectrometer (Hitachi U-3010) was used to determine the absorption peaks of the colored functionalized [2,2]paracyclophanes and the colored chemical films in Examples 1 to 4 (EX1 to EX4). The results are shown in Table 1.

TABLE 1

| | Absorption peak (nm) | |
|---|---|---|
| | Colored functionalized [2,2]paracyclophane | Colored chemical film |
| EX1 | 384 | 401 |
| EX2 | 315 | 363 |
| EX3 | 363 | 408 |
| EX4 | 393 | 421 |

Referring to Table 1, the absorption peaks of the colored functionalized [2,2]paracyclophanes in Examples 1 to 4 fall within the wavelength range of blue-violet light, indicating that the colored functionalized [2,2]paracyclophanes absorbs blue-violet light and reflects yellow light after exposure to white light, and thus, the color of the colored functionalized [2,2]paracyclophanes as seen by the naked eye is yellow.

Referring to Table 1, the absorption peaks of the colored chemical films in Examples 1, 3, and 4 fall within the wavelength range of blue light, indicating that the colored chemical films absorbs blue light and reflects yellow light after exposure to white light, and thus, the color of the colored chemical films as seen by the naked eye is yellow.

Referring to Table 1, the absorption peak of the colored chemical film in Example 2 falls within the wavelength range of blue-violet light, indicating that the colored chemical film absorbs blue-violet light and reflects yellow light after exposure to white light, and thus, the color of the colored chemical film as seen by the naked eye is yellow.

In summary, by functionalizing [2,2]paracyclophane with the functional groups of formula (A1), formula (A2), or formula (A3), the colored functionalized [2,2]paracyclophane of this disclosure possesses color, and the colored chemical film of this disclosure, which is formed from the colored functionalized [2,2]paracyclophane, possesses color that can be seen by the naked eye. Therefore, the colored chemical film can be inspected using naked eye straightaway after being processed without requiring use of an inspection equipment. Moreover, the colored chemical film can be applied as a surface coating of medical equipments to identify medical equipment according to their color, such as how and when to use such medical equipment based on directionality, for example, order, orientation, chirality, etc., which in turn helps to reduce the frequency of incorrect use of such medical equipment.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A colored functionalized [2,2]paracyclophane having formula (I):

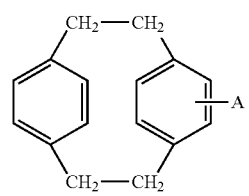

(I)

wherein,

A represents a group having formula (A1), formula (A2), or formula (A3):

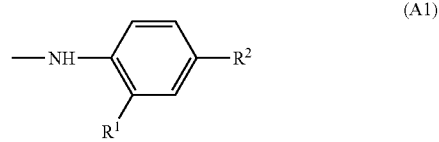

(A1)

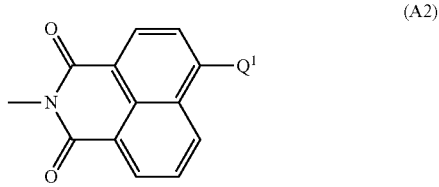

(A2)

-continued

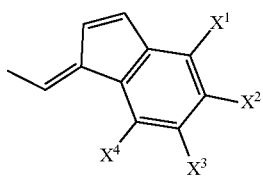
(A3)

wherein,
R¹ and R² each independently represent —H, —NO₂, —CN, or —SO₂CH₃, with the proviso that R¹ and R² are not —H at the same time;
Q¹ represents

or —N(C$_n$H$_{2n+1}$)(C$_m$H$_{2m+1}$), wherein m and n each independently represent an integer of 1 to 4; and
X¹, X², X³, and X⁴ each independently represent —H, —F, —Cl, —Br, or —I, with the proviso that X¹, X², X³, and X⁴ are not —H at the same time.

2. The colored functionalized [2,2]paracyclophane as claimed in claim 1, wherein R¹ represents —H, and R² represents NO₂, —CN, or —SO₂CH₃.

3. The colored functionalized [2,2]paracyclophane as claimed in claim 2, wherein R¹ represents —H, and R² represents —NO₂ or —CN.

4. The colored functionalized [2,2]paracyclophane as claimed in claim 1, wherein Q¹ represents

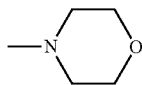

or —N(C$_n$H$_{2n+1}$)(C$_m$H$_{2m+1}$), wherein m and n each independently represent an integer of 1 to 2.

5. A colored chemical film, comprising a functionalized poly-p-xylylene having formula (II):

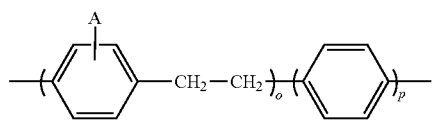
(II)

wherein
o and p each independently represent an integer of 2 to 10,000; and
A represents a group having formula (A1), formula (A2) or formula (A3):

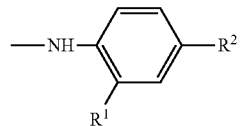
(A1)

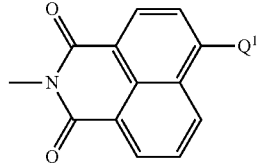
(A2)

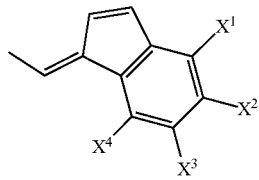
(A3)

wherein,
R¹ and R² each independently represent —H, —NO₂, —CN, or —SO₂CH₃, with the proviso that R¹ and R² are not —H at the same time;
Q¹ represents

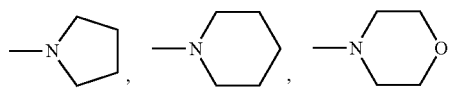

or —N(C$_n$H$_{2n+1}$)(C$_m$H$_{2m+1}$), wherein m and n each independently represent an integer of 1 to 4; and
X¹, X², X³, and X⁴ each independently represent —H, —F, —Cl, —Br, or —I, with the proviso that X¹, X², X³, and X⁴ are not —H at the same time.

6. The colored chemical film as claimed in claim 5, wherein R¹ represents —H, and R² represents —NO₂, —CN, or —SO₂CH₃.

7. The colored chemical film as claimed in claim 6, wherein R¹ represents —H, and R² represents —NO₂ or —CN.

8. The colored chemical film as claimed in claim 5, wherein Q¹ represents

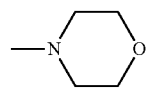

or —N(C$_n$H$_{2n+1}$)(C$_m$H$_{2m+1}$), wherein m and n each independently represent an integer of 1 to 2.

* * * * *